(12) United States Patent
Jaunky et al.

(10) Patent No.: US 9,556,400 B2
(45) Date of Patent: Jan. 31, 2017

(54) 5,5-DIMETHYL-2-PROPYL-HEXAHYDRO-2,4A-METHANO-NAPHTHALEN-1-ONE AS A FRAGRANCE AGENT

(71) Applicant: V. MANE FILS, Le Bar sur Loup (FR)

(72) Inventors: Piotr Jaunky, Chateauneuf (FR); Jean-Jacques Chanot, Speracedes (FR); Jean Mane, Magagnosc (FR)

(73) Assignee: V. MANE FILS, Le Bar sur Loup (FR)

( * ) Notice: Subject to any disclaimer, the term of this patent is extended or adjusted under 35 U.S.C. 154(b) by 46 days.

(21) Appl. No.: 14/361,900

(22) PCT Filed: Nov. 29, 2012

(86) PCT No.: PCT/FR2012/052758
§ 371 (c)(1),
(2) Date: May 30, 2014

(87) PCT Pub. No.: WO2013/079876
PCT Pub. Date: Jun. 6, 2013

(65) Prior Publication Data
US 2014/0323387 A1 Oct. 30, 2014

(30) Foreign Application Priority Data
Dec. 2, 2011 (FR) ...................................... 11 61092

(51) Int. Cl.
*C11B 9/00* (2006.01)
*C07C 49/453* (2006.01)

(52) U.S. Cl.
CPC ........... *C11B 9/0053* (2013.01); *C07C 49/453* (2013.01); *C11B 9/0042* (2013.01); *C07B 2200/07* (2013.01); *C07C 2103/66* (2013.01)

(58) Field of Classification Search
CPC ............................. C11B 9/0053; C07C 49/453
See application file for complete search history.

(56) References Cited

U.S. PATENT DOCUMENTS 4,250,338 A * 2/1981 Sprecker ................ A24B 15/30
424/69
5,015,761 A * 5/1991 Lenselink ............... C07C 29/40
512/15

OTHER PUBLICATIONS

Kraft, et al. "Odds and Trends: Recent Developments in the Chemistry of Odorants", 2000, pp. 2980-3010, vol. 39, Angew. Chem. Int. Ed.
International Search Report for PCT/FR2012/052758 dated Feb. 21, 2013.

* cited by examiner

*Primary Examiner* — Ling Choi
*Assistant Examiner* — Lanee Reuther
(74) *Attorney, Agent, or Firm* — B. Aaron Schulman, Esq.

(57) ABSTRACT

The invention relates to a compound of general formula (I) shown hereafter:

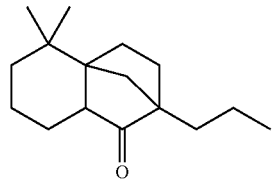

(I)

as well as a composition comprising at least said compound of general formula (I), and its uses in perfumery.

12 Claims, No Drawings

5,5-DIMETHYL-2-PROPYL-HEXAHYDRO-2,4A-METHANO-NAPHTHALEN-1-ONE AS A FRAGRANCE AGENT

The present invention relates to novel ketone compounds, as well as their uses in the chemical industry, and in particular in perfumery, cosmetics, and in the detergents industry, said compounds having a special fragrance and persistence.

The perfume industry is always searching for novel organoleptic compounds which have an intense olfactory power, whilst having production costs which are as low as possible. More particularly, compounds having pure, linear and dominant amber notes are rare and difficult to obtain. Indeed, the majority of the odorising compounds having amber notes also have tobacco, woody-pine notes (Angew. Chem. Int. Ed. 2000, 39, 2980-3010), and it is consequently difficult to obtain pure dominant amber notes which have a strong substantivity.

Following extensive research on ethers, ketones, and cyclic ketals, which are compounds well-known for having notes which are similar to amber notes (Angew. Chem. Int. Ed. 2000, 39, 2980-3010), the Applicant discovered a compound of the following general formula (I),

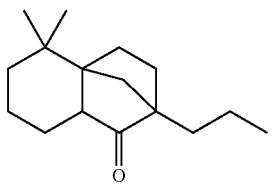

(I)

referred to as 5,5-Dimethyl-2-propyl-hexahydro-2,4a-methano-naphthalen-1-one, said compound exhibiting linear, pure, amber dominant notes, and above all having a strong persistence and therefore a strong substantivity. In addition to the organoleptic qualities mentioned above, the compound according to the present invention offers the advantage of being easily obtained with the aid of a simple and economical synthesis process.

Similar structures, or even Markush formulae which integrate the compound of formula (I) of the present invention, have been disclosed in the prior art, particularly in patents EP 0029259 and U.S. Pat. No. 4,250,338. However the compound of formula (I) of the present invention has never itself been described or synthesised previously. In these two patents EP 0029259 and U.S. Pat. No. 4,250,338 compounds of the following formula (II) are disclosed in which formula R1-R3 represent a hydrogen, or a group comprising 1 to 3 carbons.

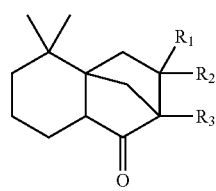

(II)

The compounds described in these two patents develop odours which are multi-faceted, but marked by a strong woody odour which is always accompanied by undesirable camphorated notes. Furthermore, in patents EP 0029259 and U.S. Pat. No. 4,250,338 it is described that, in order to develop amber notes, the disclosed ketone compounds had to be subjected to other process steps in order to obtain the corresponding alcohol, acetate or methyl ether derivatives, which entails a longer synthesis process and therefore higher costs. Finally, said derivatives nevertheless always have multifaceted odours.

Thus, a first object of the application relates to a compound of the following general formula (I):

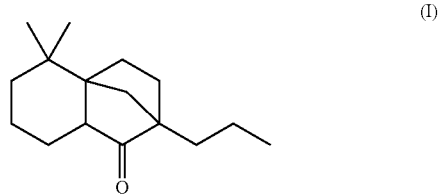

(I)

as well as its stereoisomers.

A second object of the present application relates to a composition comprising at least one compound of formula (I) or one of its stereoisomers or a mixture of these.

Finally, a last object of the present application relates to the use of at least one compound of formula (I) or one of its stereoisomers, as a fragrant agent or compound.

Table 1 below relates to a process of synthesizing the compounds of formula (I) and its stereoisomers.

The compound of formula (I) according to the present invention has the advantage of exhibiting a very dominant, linear, pure amber odour which is very persistent. The compound according to the invention is characterised on the one hand by the fact that it does not give off any undesirable camphorated note and on the other hand by a very strong substantivity. Indeed, the compound of the present invention is characterised by a persistence much more substantial than that of the similar compounds of the prior art which have dominant amber notes: said persistence is approximately two weeks for the compound of formula (I) compared to that of other molecules of the prior art for which the persistence is less than one week.

More particularly, the compound of formula (I) is characterised in that the decalin group is in a cis configuration (Ia) or (Ib).

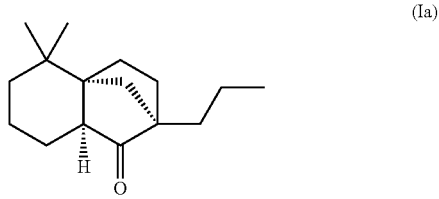

(Ia)

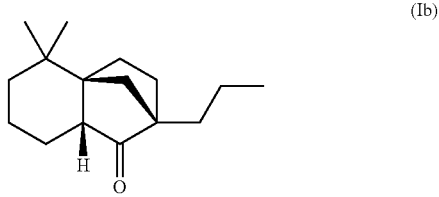

(Ib)

In another embodiment, the decalin group of the compound of formula (I) is in a trans configuration (Ic) or (Id).

(Ic)

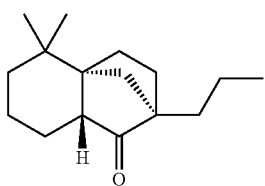

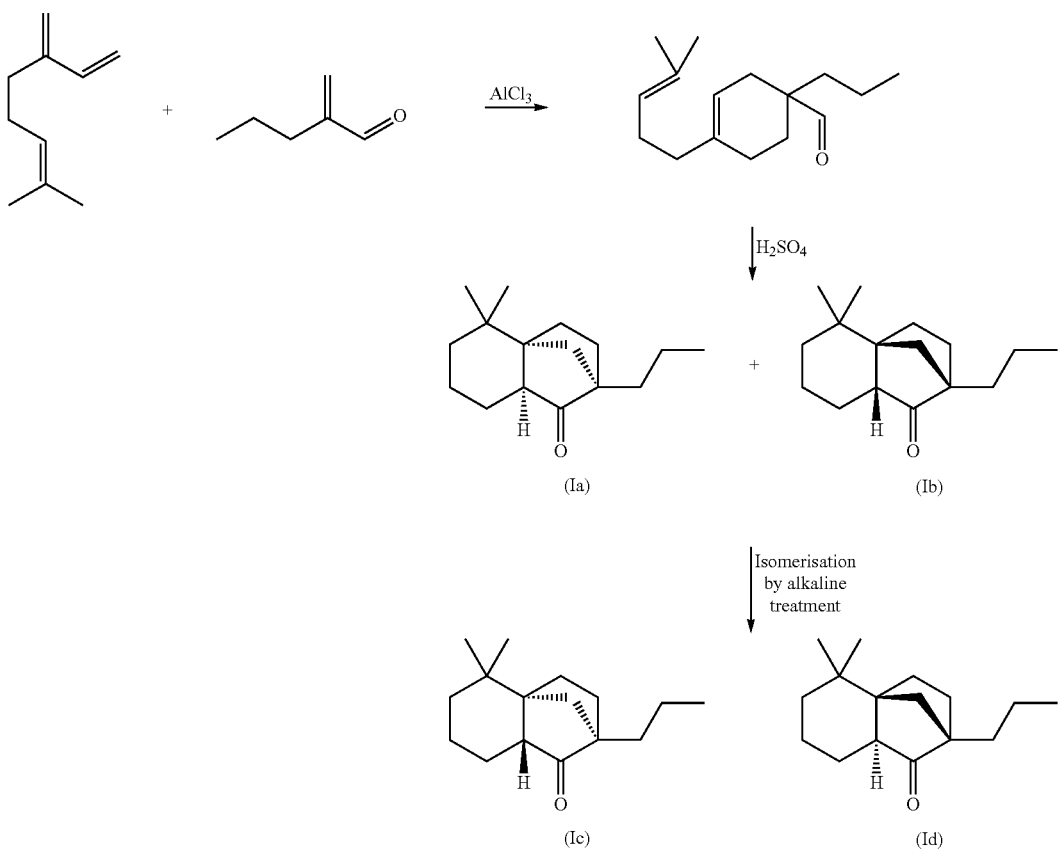

Table 1: Process of synthesizing compounds (Ia), (Ib), (Ic) and (Id)

Once the cis-decalin compounds (Ia) and (Ib) are obtained, these can be transformed into trans-decalin derivatives (Ic) and (Id) by simple methods known to the person skilled in the art (for example alkaline treatment).

In the two cases, the synthesised compounds have fresh linear amber notes.

A second object of the present invention relates to a composition comprising at least one compound of general formula (I), (Ia), (Ib), (Ic) or (Id) in the form of a stereoisomer or a mixture of stereoisomers or a racemic mixture.

According to one particular embodiment, the composition is characterised in that it further comprises at least one other odorising substance.

The effective quantity of the compounds of formula (I) according to the invention incorporated into the composition will vary according to the nature of the composition, the desired odorising effect, and the nature of the other odorising form of a racemic mixture of the cis-decalin compounds (Ia) and (Ib).

The compound of formula (I) according to the present invention can be obtained via a simple and economic process of synthesis, as opposed to all of the long and costly processes which allow amber notes to be obtained. For example, a racemic mixture of the compounds (Ia) and (Ib) (then (Ic) and (Id) is obtained simply and directly by a Diels-Alder reaction making myrcene and 2-methylene pentanal react, followed by an acid treatment. Table 1 below reflects the main steps of this synthesis.

-continued (Id)

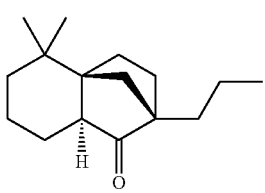

By decalin, we mean a bicyclic organic compound, also called decahydronaphthalene.

In a preferred embodiment, the compound according to the invention is of formula (Ia) or (Ib). Preferably, the compound according to the invention is present in the or non-odorising compounds possibly present, and will be able to be easily determined by the person skilled in the art, in the knowledge that it can vary in a very wide range, from 0.1 to 99% by weight, in particular from 0.1 to 50% by weight, notably from 0.1 to 30% by weight relative to the total weight of the composition.

The invention also relates in particular to a cosmetic composition, notably face and body cream, talcum powder, oil for the hair or for the body, shampoo, hair lotion, bath salts, bath oil, shower gel, bath gel, toilet soap, body antiperspirant, body deodorant, lotions, shaving cream, shaving soap, cream, toothpaste, mouthwash, pomade comprising at least one compound of formula (I), or at least one composition comprising at least one compound of the formula (I).

The invention also relates to a household product, notably softener, detergent, washing powder, room deodorising products, comprising at least one compound of formula (I) or at least one composition comprising at least one compound of the formula (I).

The compound(s) according to the invention can be used, alone or in combination, by themselves or can be incorporated in or on an inert support material or which can contain other active ingredients of the end composition. A great variety of support materials can be used including, for example, polar solvents, oils, fats, finely divided solids, cyclodextrins, maltodextrins, gums, resins and any other support material known for such compositions.

The last object of the invention is the use of at least one compound of formula (I) according to the invention as a fragrant agent or compound, as an odour-masking agent or as an odour-neutralising agent. The term "fragrant" is used here to designate any organoleptic compound which pleasantly stimulates the sense of smell. The term "masking agent" or "masking" is understood to mean reducing or eliminating the perception of a bad odour generated by one or more molecules entering into the composition of a product.

Furthermore, said compound can be used alone or in combination with at least one other aromatic or perfuming ingredient, and/or at least one solvent, and/or at least one adjuvant. The supplementary odorising agent(s) can be compounds of formula (I) or other odorising agents known to the person skilled in the art who will be in a position to make a choice according to the effect sought.

The compounds according to the invention will generally be used in the field of perfumery. "Perfumery" means not just perfumery in the conventional sense of the term but also the other fields in which the odour of products is important. They can be perfumery compositions in the conventional sense of the term, such as perfuming bases and concentrates, eaux de Cologne, eaux de toilette, perfumes, and similar products; topical compositions—in particular cosmetic compositions—such as face and body creams, talcum powders, oils for the hair, shampoos, hair lotions, bath salts and bath oils, shower gels and bath gels, toilet soaps, body antiperspirant and deodorants, shaving lotions and creams, soaps, creams, toothpastes, mouthwashes, pomades and similar products; and household products such as softeners, detergents, washing powders, room deodorisers, and similar products.

A particular embodiment of the invention lies in the use of a racemic mixture comprising the cis-decalin compounds (Ia) and (Ib) to modify or reinforce the organoleptic properties of a substance, a composition, or an article.

"Organoleptic properties" is understood to mean any property capable of modifying, improving or strengthening the organoleptic perception of a substance, a composition or an article by a user. Thus, by way of preferred example, the organoleptic agent according to the invention can consist of a perfuming agent capable of conferring, modifying, improving or strengthening the olfactory perception of a substance, a composition or an article.

The general principle of the invention resides in the preparation and use of the previously described compounds of formula (I) in perfumery. The following examples illustrate a particular way of preparing the compounds of the invention as well as the olfactory profile of each of the exemplified compounds. These examples are given merely with the aim of illustration and must not be understood to be limiting the general scope of the invention.

EXAMPLE 1

Comparison of the Olfactory Evaluations of the Compound of Formula (I) Relative to the Compounds of the Prior Art

| Disclosed compounds or compounds of the invention | Olfactory evaluation of the compounds disclosed in patent EP 0029259 | Olfactory evaluation of the compounds disclosed in patent U.S. Pat. No. 4,250,338 | Olfactory evaluation by MANE of the compounds of the prior art and the present invention |
|---|---|---|---|
| 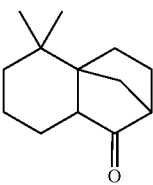 | Woody, green, minty, camphorated | Woody camphorated, sweet with minty and amber traces | Aromatic, camphorated, sweet, slightly earthy |
| 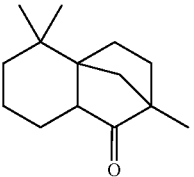 | Green, camphorated, woody | Woody, with green, acid, cardamom traces | Camphorated, woody, resinous traces |

| Disclosed compounds or compounds of the invention | Olfactory evaluation of the compounds disclosed in patent EP 0029259 | Olfactory evaluation of the compounds disclosed in patent U.S. Pat. No. 4,250,338 | Olfactory evaluation by MANE of the compounds of the prior art and the present invention |
|---|---|---|---|
| 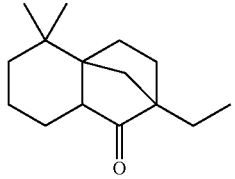 [SMILES: CCC12CCC3(C1)C(CCCC3(C)C)C2=O] | | | Very weak, practically odourless |
| 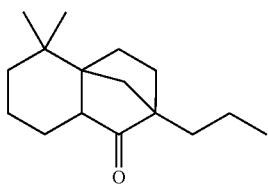<br>I/Ib<br>CIS-decalin configuration | | | Warm rich amber notes, clean, powerful without camphorated or earthy notes. Linear and very persistent notes |
| 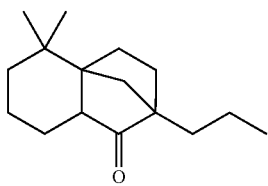<br>Ic/Id<br>TRANS-decalin configuration | | | Same olfactory evaluation as that for cis-decalin compound, but with a weaker intensity |

EXAMPLE 2

Olfactory Evaluation of the Ketone Compounds of the Prior Art Relative to the Compound According to the Invention

| Disclosed compounds or compounds of the invention | Olfactory evaluation of the compounds disclosed in patent EP 0029259 | Olfactory evaluation of the compounds disclosed in patent U.S. Pat. No. 4250338 | Olfactory evaluation by MANE of the compounds of the prior art and the present invention |
|---|---|---|---|
| 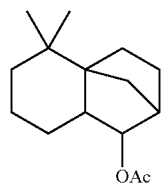 [SMILES: CC(=O)OC1C2CCC3(C2)C1CCCC3(C)C] | amber, woody | dry woody (cedar, vetiver), amber-type and sandalwood type aromas | |
| 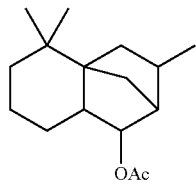 [SMILES: CC(=O)OC1C2CC3(CC2C)C1CCCC3(C)C] | amber, woody | | |

-continued

| Disclosed compounds or compounds of the invention | Olfactory evaluation of the compounds disclosed in patent EP 0029259 | Olfactory evaluation of the compounds disclosed in patent U.S. Pat. No. 4250338 | Olfactory evaluation by MANE of the compounds of the prior art and the present invention |
|---|---|---|---|
| [structure with OH] | | dry woody, amber-type, castoreum, cedar aroma, patchouli | |
| [structure with OH] | | Woody, amber, cedar aroma with green and fruity traces | |
| [structure with OMe] | | Woody, amber, sandalwood-type and oriental aroma | |
| [structure with OMe] | | amber, woody, camphorated, aromatic sweet-fruity profile | |
| I/Ib CIS-decalin configuration | | | Warm rich amber notes, clean, powerful without camphorated or earthy notes. Linear and very persistent notes |
| Ic/Id TRANS-decalin configuration | | | Same olfactory evaluation as that for cis-decalin compound, but with a weaker intensity |

EXAMPLE 3

Synthesis of a Racemic Mixture of the Compounds (Ia) and (Ib)

Myrcene (136 g:1 mol) is reacted with 2-methylene pentanal (120 g:1.22 mol) in the presence of $AlCl_3$ (8 g) in 350 ml of toluene for 16 hours at ambient temperature. After a flash distillation (boiling point: 100° C., 1 Torr), 107 g are obtained of a material which is then subjected to a cyclisation by a treatment using $H_2SO_4$ (4 g) dissolved in 600 ml of toluene, at 60° C. for 24 hours. After purification by distillation (boiling point: 104° C., 0.8 Torr), 81 g of a compound of formula (I) are obtained. If necessary, the compound of formula (I) can be crystallised with the aid of hexane at −28° C. in order to obtain crystals with a melting point of 45° C.

Spectroscopic Analysis:

NMR $^1$H (CDCl$_3$, 200 MHz): δ 0.89 (t, 3H, J=7 Hz); 0.95 (s, 3H); 0.99 (s, 3H); 1.17-1.93 (m, 16H); 2.00-2.06 (m, 1H).

NMR $^{13}$C (CDCl$_3$, 50 MHz): δ 14.96 (q); 19.47 (t); 21.02 (t); 21.96 (t); 22.54 (t); 23.56 (q); 26.28 (q); 31.55 (t); 32.68 (t); 33.61 (s); 36.77 (t); 41.05 (t); 51.97 (s); 53.84 (d); 59.37 (s); 220.72 (s).

IR: 1465, 1730, 2870, 2934, 2960 cm$^{-1}$

MS: 234 (61, M$^{+·}$), 205 (13), 191 (40), 177 (22), 165 (14), 164 (15), 163 (22), 151 (12), 150 (40), 149 (100), 135 (29), 126 (36), 122 (30), 121 (22), 109 (76), 108 (49), 107 (30), 105 (14), 95 (15), 93 (34), 91 (36), 81 (23), 79 (35), 77 (25), 69 (11), 67 (33), 55 (24), 41 (29).

EXAMPLE 4

Synthesis of a Racemic Mixture of Compounds (Ic) and (Id)

A mixture of the compounds (Ia) and (Ib) is refluxed in methanol in the presence of KOH (10% w/w) for 24 hours until complete isomerisation into compounds (Ic) and (Id).

NMR 1H (CDCl3, 200 MHz): δ 0.89 (m, 9H); 1.12-1.85 (m, 16H); 1.89-2.00 (m, 1H).

NMR 13C (CDCl3, 50 MHz): δ 14.96 (q); 19.37 (t); 20.76 (t); 23.93 (q); 24.11 (t); 25.94 (q); 29.64 (t); 30.90 (t); 31.45 (t); 32.05 (s); 37.90 (t); 38.43 (t); 50.44 (s); 52.21 (d); 58.89 (s); 220.59 (s).

IR: 1462, 1739, 2869, 2929, 2955 cm−1.

MS: 234 (66, M+.), 205 (14), 191 (40), 177 (24), 165 (16), 164 (16), 163 (26), 151 (13), 150 (43), 149 (96), 135 (33), 126 (46), 125 (11), 123 (10), 122 (36), 121 (25), 110 (11), 109 (100), 108 (66), 107 (34), 105 (17), 95 (20), 93 (41), 91 (43), 81 (36), 80 (12), 79 (44), 77 (31), 69 (18), 67 (46), 65 (11), 55 (36), 53 (14), 43 (15), 41 (44), 39 (14).

EXAMPLE 5

Olfactory Evaluation of the Compounds (Ia) and (Ib) in Racemic Mixture

The compounds (Ia) and (Ib) were evaluated in a 50% solution of methyl myristate: an amber, intense and linear odour which lasts for a very long time (in excess of two weeks) is noted.

EXAMPLE 6

Comparative Evaluation of a Formula Comprising or Not Comprising the Compound of Formula (I)

| Substance involved | Composition 1 Parts (by weight) | Composition 2 Parts (by weight) |
|---|---|---|
| Violettyne[1] | 10 | 10 |
| Compound of formula (I)[2] | / | 60 |
| Calon 1951 Cal[3] | 10 | 10 |
| Veramoss[4] | 4 | 4 |
| Ethyl linalool[5] | 100 | 100 |
| Florol[6] | 20 | 20 |
| Methyl dihydro jasmonate[7] | 574 | 574 |
| Helional[8] | 60 | 60 |
| Iso E Super[9] | 40 | 40 |
| Lilial[10] | 20 | 20 |
| Melonal[11] | 2 | 2 |
| Methylionantheme[12] | 10 | 10 |
| Benzyl salicylate | 20 | 20 |
| Cis-3 hexenyl acetate[13][14] | 4 | 4 |
| Styrallyl acetate[14] | 10 | 10 |
| Allyl amyl glycolate[14] | 2 | 2 |
| Galbex[15] | 4 | 4 |
| Cis-3 hexenol[14] | 4 | 4 |
| Liffarome[16] | 4 | 4 |
| Triplal[14][17] | 2 | 2 |
| DPG | 100 | 40 |
| Total | 1000 | 1000 |

[1] (E)-Undeca-1,3-dien-5-yne; origin: Firmenich, Switzerland
[2] Compound of formula (I) in the form of a racemic mixture; origin: V. Mane Fils, France.
[3] 7-Methyl-benzo[b][1,4]dioxepin-3-one; origin: Symrise, Germany.
[4] 2,4-Dihydroxy-3,6-dimethyl-benzoic acid methyl ester; origin: International Flavours and Fragrances, USA.
[5] origin: Givaudan, Switzerland.
[6] 2-Isobutyl-4-methyl-tetrahydro-pyran-4-ol; origin: Firmenich, Switzerland.
[7] [3-Oxo-2-((E)-pentyl)-cyclopentyl]-acetic acid methyl ester; origin: Firmenich, Switzerland.
[8] 3-Benzo[1,3]dioxol-5-yl-2-methyl-propionaldehyde; origin: International Flavors and Fragrances, USA.
[9] 1-(2,3,8,8-Tetramethyl-1,2,3,4,5,6,7,8-octahydro-naphthalen-2-yl)-ethanone; origin: International Flavours and Fragrances, USA.
[10] 3-(4-tert-Butyl-phenyl)-2-methyl-propionaldehyde; origin: Givaudan Switzerland.
[11] 2,6-Dimethyl-hept-5-enal; origin: Givaudan Switzerland.
[12] (E)-3-Methyl-4-(2,6,6-trimethyl-cyclohex-2-enyl)-but-3-en-2-one; origin: Firmenich, Switzerland.
[13] origin: V. Mane Fils, France.
[14] 10% in dipropylene glycol.
[15] origin: Firmenich, Switzerland.
[16] Carbonic acid (E)-hex-3-enyl ester methyl ester; origin: International Flavors and Fragrances, USA.
[17] 2,4-Dimethyl-cyclohex-3-enecarbaldehyde; origin: International Flavors and Fragrances, USA.
[18] Ethoxy-methoxy-cyclododecane; origin: Henkel, Germany.

Evaluation of Composition 2/Composition 1:

Top: powerful amber-woody note from the beginning of evaporation. Strengthens the composition's fruity and green notes.

Middle and base: elegant woody and amber harmony, goes very well with the composition's sea odour, creating a unique and powerful character. Persists for a long time on a smelling strip.

The invention claimed is:

1. A compound of the following general formula (I):

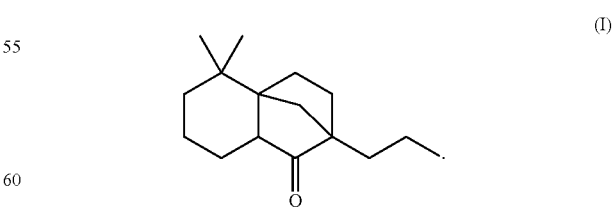

wherein the compound has an odor having no undesirable camphoraceous notes.

2. A compound according to claim 1, wherein the decalin group is in a cis configuration (Ia) or (Ib).

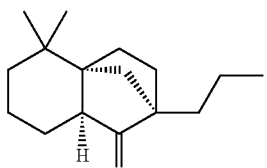
(Ia)

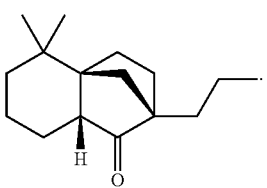
(Ib)

3. A compound according to claim 1, wherein the decalin group is in a trans configuration (Ic) or (Id).

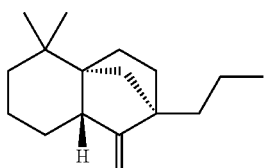
(Ic)

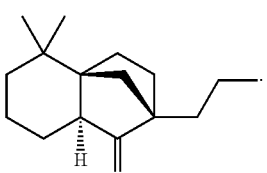
(Id)

4. A composition comprising at least one compound of general formula (I), (Ia), (Ib), (Ic) or (Id) as defined in claim 1, in the form of a stereoisomer, or a mixture of stereoisomers, or a racemic mixture.

5. The composition according to claim 4 further comprising at least one other odorizing substance.

6. The composition according to claim 4, wherein the compound is present in a concentration of between 0.1 and 99% by weight relative to the total weight of the composition.

7. The composition according to claim 6, wherein the compound is present in a concentration of between 0.1 and 30% by weight relative to the total weight of the composition.

8. A method of imparting a fragrance to a cosmetic composition or household product comprising adding at least one compound of formula (I) as defined in claim 1 as a fragrant agent to said composition or product.

9. The method according to claim 8, wherein the compound of formula (I) is used in combination with at least one other aromatic or perfuming ingredient, and/or at least one solvent, and/or at least one additive.

10. The method according to claim 8 wherein the compound confers modifies or reinforces the organoleptic properties of a substance, a composition, or an article.

11. The method according to claim 8 wherein the compound is in the form of a racemic mixture comprising the cis-decalin compounds (Ia) and (Ib), and said compound is used to modify or reinforce the organoleptic properties of a substance, a composition, or an article.

12. A method of mask ng or neutralizing an odor in a cosmetic composition or household product comprising adding at least one compound of formula (I) as defined in claim 1 as an odor-masking or odor-neutralizing agent to said composition or product.

* * * * *